(12) United States Patent
Martin

(10) Patent No.: US 7,098,361 B1
(45) Date of Patent: Aug. 29, 2006

(54) RIGID RING AMINO ACIDS AND POLYAMIDES THERE FROM

(76) Inventor: Donald H. Martin, 107 Norwood Ave, Asheville, NC (US) 28804

( * ) Notice: Subject to any disclaimer, the term of this patent is extended or adjusted under 35 U.S.C. 154(b) by 35 days.

(21) Appl. No.: 10/720,648

(22) Filed: Nov. 24, 2003

Related U.S. Application Data

(60) Provisional application No. 60/429,663, filed on Nov. 27, 2002.

(51) Int. Cl.
*C07C 229/00* (2006.01)
*C08L 77/00* (2006.01)

(52) U.S. Cl. ........................................ 562/507; 528/328
(58) Field of Classification Search ................ 562/507; 528/328
See application file for complete search history.

(56) References Cited

U.S. PATENT DOCUMENTS 2,868,770 A    1/1959   Temin

FOREIGN PATENT DOCUMENTS

DE          3829455 A1  *  3/1990
JP          49041355       11/1974
JP          49041355 B4  * 11/1974

OTHER PUBLICATIONS

Jean Colonge & Edouard Fichet ; The Polyamidification of Several p-Aminophenyl Carboxylic Acids,Bulletin de la Societe Chimique de France, pp. 412-419 (1955).
M. Levine & S.C. Temin ; Isomorphous Replacement in a Copolyamide System; J. Polymer Sci. 49, p. 291-6(1961).
R.S. Muromova, et al ; Synthesis of Amino Acids of the Cyclohexane Series and Polyamides Based on Them; Konf. po Vysokomolekul Soedin, pp. 220-225 (1962).
R.S. Muromova et al; New Polyamids and Fibers Based on ω-Amino Acids Containing Cyclohexane Rings in the Main Chain; Khimicheskie Volokna, 4, pp. 69-73 (1967).
R.S. Muromova; Fiber Based on Trans-Beta-(4-Aminocyclohexyl)propionic and Zeta-Aminoenanthic Acids, Khimicheskie Volokna, 5, p. 70-1 (1968).

* cited by examiner

*Primary Examiner*—Ana Woodward

(57) ABSTRACT

This invention is a family of α,ω amino acids based on 1,4 substituted rigid ring structures and the useful polyamides made from them.

3 Claims, 2 Drawing Sheets

Structure of Rigid Ring Amino Acids

Figure 1:
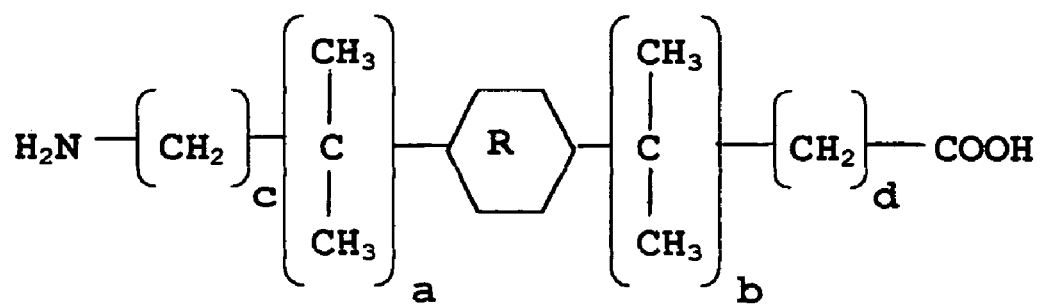

Structures of Rigid Ring Amino Acid Sub-families

| Structure | Sub-family Designation |
|---|---|
| 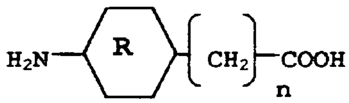 | An |
| 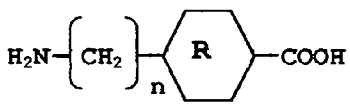 | Bn |
| 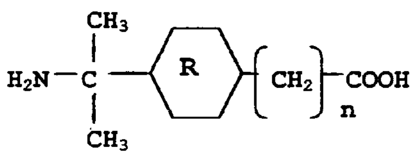 | Cn |
| 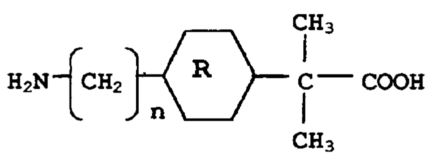 | Dn |
| 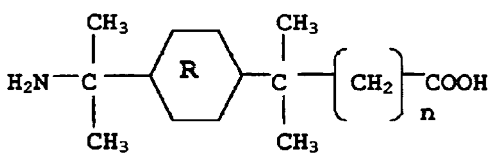 | En |
| 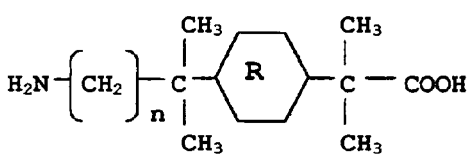 | Fn |
| 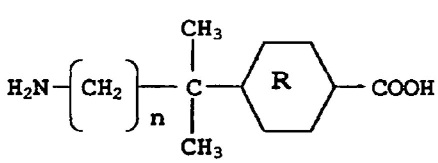 | Gn |
| 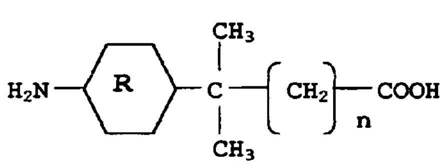 | Hn |

RIGID RING AMINO ACIDS AND POLYAMIDES THERE FROM

RELATED APPLICATION

This application is entitled to the benefit of Provisional Patent Application 60/429,663 filed 2002, Nov. 27.

BACKGROUND OF THE INVENTION

Polyamides are well known and useful materials utilized throughout the world. The variations in their material properties are influenced by their polymer structures. Their polymer structures are influenced by the chemical nature and structure of the polymer's monomer units and the way in which the monomer units are joined in the polymer.

The term nylon is embraced within the broader class of polyamides. It is most commonly applied to those polyamides which are melt processable such as nylon 6,6 and nylon 6. Such thermoplastic polyamides are distinguishable from polyamides which are not melt processable such as polyparaphenylene terephthalamide. The monomers for polyamides are generally either a diamine and a dicarboxylic acid or an amino acid. A diamine and a dicarboxylic acid lead to a nylon noted as AABB such as nylon 6,6 made from 1,6 diaminohexane and adipic acid. An amino acid or its lactam leads to a nylon noted as AB such as nylon 6 made from 6-aminohexanoic acid or its lactam, caprolactam.

The largest usage AB type nylon is that made from caprolactam which is known worldwide as nylon 6. This polymer has a relatively simple chemical structure. Its structure is an aliphatic repeat unit of 5 methylene units joined by an amide unit. Homologs of this polymer have also been explored and developed. Two homologs which are commercially available polymers are nylon 11 and nylon 12 in which the number of methylene groups is 10 and 11 respectively. These nylons have a longer methylene chain length and a lower ratio of amide groups to methylene groups than nylon 6,6 or nylon 6. Polymers such as nylon 11 and nylon 12 derive much of their value from their reduced moisture sensitivity compared to nylon 6,6 or nylon 6. However, the longer methylene component of these polymers also results in reduced melting points such as about 190 C and 180 C for nylon 11 and nylon 12 respectively.

These melting points can be compared to about 225 C for nylon 6 and 265 C for nylon 6,6. Their lower melting points limit these longer chain nylons from applications in which they might otherwise provide a good balance of properties. Such applications are many industrial fiber applications or molded articles in high temperature environments. Melt processable polymers which have the properties to fit these more stringent thermal and mechanical requirements are often termed engineering thermoplastics.

Polymers in the categories of nylons, polyolefins, and polyesters derive many of their useful properties from being semi-crystalline materials. This term denotes the fact that in the solid state many of the chains of these polymers align into spatially regular structures which are crystalline regions. Such regularity is revealed by, for example, patterned diffraction of x-rays. The remainder of the polymer chains are disordered forming what is termed the amorphous regions. The amount of crystalline content of these polymers covers a wide range with most falling within the range of approximately 20% to 80%.

Useful semi-crystalline engineering thermoplastics are bounded by both lower and upper melting points. Lower melting points limit applications whereas higher melting points introduce problems such as increasing degradation at the higher temperatures required in processing and fabrication. A useful range for the melting temperature for a wide variety of engineering thermoplastics is approximately 200 C to 300 C.

Partial substitution of an alternate minor monomer for the predominate monomer in semi-crystalline polymers normally results in a reduction in melting point. One somewhat uncommon phenomenon occurs in which a second monomer unit fits into a polymer's crystal lattice in the place of a predominant first monomer. Substitutable monomers of this type are often termed isomorphous (Kohan, pp. 370–374). The substitution of an isomorphous monomer normally produces a monotonic and continuous melting point behavior over the range of monomer concentrations.

One approach to increasing the melting points of aliphatic nylons is the incorporation of comonomers with rigid units such as phenyl or cyclohexyl into the polymer chain. If these units are isomorphic with the aliphatic units which they replace, the melting point of the polymer can be increased with little, if any, sacrifice in crystallinity (J. Ridgway, J. Polym. Sci., A-1, vol. 8, pp. 3089–3111, 1970). This phenomenon has been explored much more widely in the AABB type nylons than in the AB type nylons.

A desirable goal would be a family of AB type nylons with longer methylene lengths having reduced moisture sensitivity such as those of nylons 11 and 12 but with higher melting temperatures. Such higher melting temperatures would allow use in higher temperature applications. This invention describes compositions which achieve an improved combination of lower moisture absorption with a useful range of melting points in a family of AB type nylon polymers.

SUMMARY OF THE INVENTION

This invention describes a family of $\alpha,\omega$ amino acids based upon 1,4 substituted rigid rings which are either phenyl or cyclohexyl. One object of this invention is the use of these amino acids as monomers for AB type polyamides having useful combinations of properties and particularly low moisture absorption at useful melting points. A further object of this invention is the use of these amino acids as comonomers with aliphatic amino acids and lactams. A yet further use of selected amino acids of this invention is as isomorphic comonomers with selected aliphatic amino acids and lactams.

BRIEF DESCRIPTION OF THE DRAWING FIGURES

FIG. 1 is a general formula and structure for the compositions of Rigid Ring Amino Acids of this invention encompassing values for the indices a, b, c, and d as described in the Specification.

Figure 2:
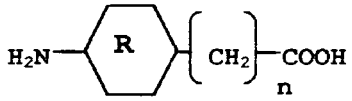
Figure 2:
Figure 2:
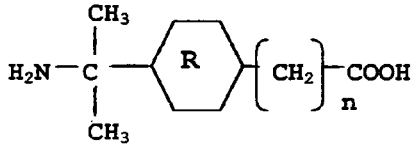
Figure 2:
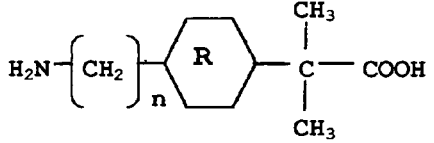
Figure 2:
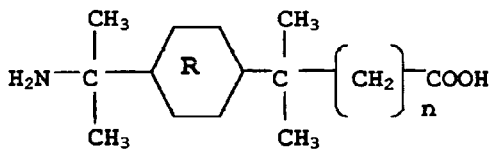
Figure 2:
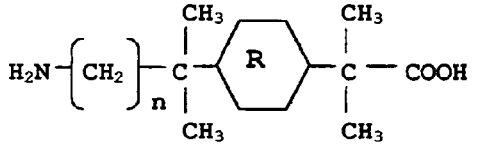
Figure 2:
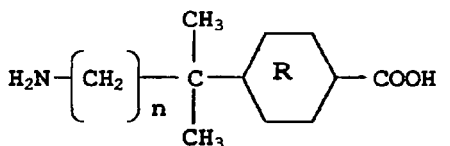
Figure 2:
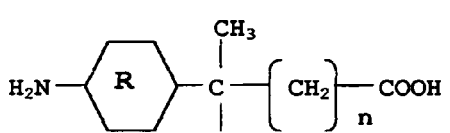

FIG. 2 summarizes the formulae and structures of each sub-category of the general structure of FIG. 1. Each sub-category is also specified by the allowable indices described in the Specification and shown in Table 1.

DETAILED DESCRIPTION OF THE INVENTION

Structures of Rigid Ring Amino Acids

The general structure of the amino acids of this invention is shown in FIG. 1. As used herein, an amino acid as described in FIG. 1 is defined as a Rigid Ring Amino Acid. The rigid ring, as denoted by R in FIG. 1, can be either a phenyl unit or a cyclohexyl unit. Distinctions can be made between the amino acids based upon the two alternative ring structures by designating them as phenyl based Rigid Ring Amino Acids or cyclohexyl based Rigid Ring Amino Acids.

In addition to the designation of the rigid ring unit, four parameters define the composition of each of the amino acids of this invention. These parameters are the four indices a, b, c, and d as shown in FIG. 1.

The indices a and b can have the value of either 1 or 0. The indices c and d are selected such that their product is 0. For any non-zero c the associated d value is 0 and for any non-zero d value the associated c value is 0. One alternative is that both c and d are 0.

The carboxyl and amine groups are $\alpha,\omega$ for each member of this family. The rigid rings are 1,4 substituted.

The members of this family of Rigid Ring Amino Acids are further described by quantitative parameters defined as follows:

Effective Methylene Length (EML):

The Effective Methylene Length is the number of consecutive chain carbon atoms between the carboxyl group and the amine group of the amino acid. For purposes of this parameter a 1,4 substituted phenyl or cyclohexyl moiety is counted as making a contribution to the Effective Methylene Length of 4 units.

Carbon Number (CN):

The Carbon Number is the total number of carbon atoms in the amino acid molecule.

The cyclohexyl based amino acids of this invention have the general molecular formula of $C_{(x)}H_{(2x-1)}NO_2$.

The phenyl based amino acids of this invention have the general molecular formula of $C_{(x)}H_{(2x-7)}NO_2$.

The allowable options for the indices shown in FIG. 1 can be tabulated as shown in Table 1. The options for the indices a and b are either 0 or 1. The options for the indices c and d are either 0 or n. The index n is a positive integer which can also be 0. These combinations describe a sub-family of eight general structures noted as A through H. Use of this letter designation plus a value for the index n yields a two term symbol which designates unambiguously the structure of each compound once the designation of the rigid ring as either phenyl or cyclohexyl is made.

TABLE 1

Rigid Ring Amino Acid Composition Indices and Sub-families

| Index Values | | | | Rigid Ring Amino Acid | Two Term |
| --- | --- | --- | --- | --- | --- |
| a | b | c | d | Sub-family | Symbol |
| 0 | 0 | 0 | n | A | An |
| 0 | 0 | n | 0 | B | Bn |
| 1 | 0 | 0 | n | C | Cn |
| 1 | 0 | n | 0 | G | Gn |
| 0 | 1 | 0 | n | H | Hn |
| 0 | 1 | n | 0 | D | Dn |
| 1 | 1 | 0 | n | E | En |
| 1 | 1 | n | 0 | F | Fn |

The general structures of these sub-families of Rigid Ring Amino Acids are shown in FIG. 2. Classifying these amino acids into the sub-families of A through H with the index number n for the methylene length shown provides a convenient and unambiguous two term coding system. By way of illustration, the cyclohexyl based Rigid Ring Amino Acid with the symbol A5 has the general structure A shown in FIG. 2 with a rigid ring of cyclohexyl and with the number of methylenes equal to 5. It has an Effective Methylene Length of 9 and a Carbon Number of 12.

The structures of the Rigid Ring Amino Acids in sub-families C, D, E, F, G, and H all have at least one dimethyl substituted carbon atom adjacent to the ring. This dimethyl substitution provides a hindrance to rotation about the carbon to ring bond. Therefore these structures are further defined as Hindered Rigid Ring Amino Acids. They can be yet further defined based upon the nature of the rigid ring as either a phenyl based Hindered Rigid Ring Amino Acid or a cyclohexyl based Hindered Rigid Ring Amino Acid. A yet further distinction among the Hindered Rigid Ring Amino Acids can be made between those in which only one of the carbons adjacent to the ring is dimethyl substituted such as sub-families C, D, G, and H versus those in which both carbons adjacent to the ring are dimethyl substituted such as sub-families E and F. Such structures can be described as monohindered and dihindered respectively.

Pairs of Rigid Ring Amino Acids can be chosen such that a Rigid Ring Amino Acid with the amine group adjacent to the rigid unit can be paired with another Rigid Ring Amino Acid with a carboxyl group adjacent to the rigid unit. An example of such a pairing would be a Rigid Ring Amino Acid from sub-family A with a Rigid Ring Amino Acid from sub-family B. A polyamide made with such a pair has the potential for an amide formed with an extended length rigid unit. Such an extended unit has two rigid ring units joined by the rigid amide group. A pair of Rigid Ring Amino Acids chosen such that for the first the amine group is adjacent to the rigid ring and for the second the carboxylic acid group is adjacent to the rigid unit is, as used herein, defined as an Asymmetric Rigid Ring Amino Acid Pair. Further, for purposes of definition of an Asymmetric Rigid Ring Amino Acid Pair as used herein, an amine group or a carboxylic acid group attached to a dimethyl substituted carbon atom adjacent to the rigid ring is considered adjacent to the rigid ring. Such Rigid Ring Amino acids are those in the sub-families of C, D, E, F, G and H. For polyamides made with Asymmetric Rigid Ring Amino Acid Pairs it is preferable that both amino acids be cyclohexyl based. The extended length rigid unit enabled by an Asymmetric Rigid Ring Amino Acid Pair is useful in polyamides. It can influence polymer structure or behavior such as accelerated nucleation upon crystallization.

It is also recognized that Rigid Ring Amino Acids and their derivatives, such as their sulfonamides, would be expected to have useful biological activity depending upon the particular compound and its application.

Synthesis of Rigid Ring Amino Acids

To those knowledgeable in the art, it is apparent that the family of compounds described in this invention has a variety of synthesis routes. The synthesis routes described in the following were chosen because they utilize many common starting materials, synthesis steps, intermediates and characterization methodology thereby making the synthesis processes for members of this family more general. Any particular Rigid Ring Amino Acid may have an alternate synthesis route which may be preferred for either technical reasons or economic reasons. This may typically be the case for those Rigid Ring Amino Acids with relatively short methylene lengths in which n=0 or 1 or 2 or 3.

It is recognized that in the synthesis routes described below the final product in each case is the cyclohexyl based Rigid Ring Amino Acid. However, the phenyl based Rigid Ring Amino Acid is a precursor product and could be utilized in many applications. For their performance in polyamides, the cyclohexyl based Rigid Ring Amino Acids are preferred over the phenyl based Rigid Ring Amino Acids.

All of the steps in the synthesis routes in the following are well known in organic chemistry and are described in several advanced organic chemistry texts. As an aid to describing the synthesis steps shown, reference is made to the text, "Advanced Organic Chemistry", 3rd Edition by Jerry March, John Wiley and Sons (1985). Each synthesis step is referenced with the designation of the pages of this text which treat that particular organic chemistry reaction or process.

Synthesis steps for Rigid Ring Amino Acids An where n=number of methylenes defined in FIG. 2:

1. Friedel Crafts mono acylation of benzene with a diacid of structure $HOOC(CH_2)_mCOOH$ (m=n−1 for n>2) [March, pp. 484–487]

2. Reduction of the keto group to a methylene [March, pp. 1096–1098]

3. Nitration of the phenyl ring [March, pp. 468–470]

4. Reduction of the nitro group to an amine [March, p. 1103]

5. Reduction of the phenyl ring to cyclohexyl [March, pp. 700–702]

Synthesis steps for Rigid Ring Amino Acids Bn where n=number of methylenes defined in FIG. 2:

1. Friedel Crafts mono acylation of benzyl alcohol with a diacid of structure $HOOC(CH_2)_mCOOH$ (where m=n−2 for n>3) [March, pp. 484–487]

2. Reduction of the keto group to a methylene [March, pp. 1096–1098]

3. Amination of the free carboxylic acid group to an amide [March, pp. 371–374]

4. Oxidation of the alcohol group to a carboxylic acid group [March, p. 1084]

5. Reduction of the amide to an amine [March, pp. 1099–1100]

6. Reduction of the phenyl ring to cyclohexyl [March, pp. 700–702]

Synthesis steps for Rigid Ring Amino Acids Cn where n=number of methylenes defined in FIG. 2:

1. Friedel Crafts mono acylation of benzene with a diacid of structure $HOOC(CH_2)_mCOOH$ (m=n−1 for n>2) [March, pp. 484–487]

2. Reduction of the keto group to a methylene [March, pp. 1096–1098]

3. Friedel Crafts alkylation of the phenyl ring with 2-bromo-2-nitropropane [March, pp. 479–484]

4. Reduction of the nitro group to an amine [March, p. 1103]

5. Reduction of the phenyl ring to cyclohexyl [March, pp. 700–702]

Synthesis steps for Rigid Ring Amino Acids Dn where n=number of methylenes defined in FIG. 2:

1. Friedel Crafts mono acylation of benzene with a diacid of structure $HOOC(CH_2)_nCOOH$ (m=n−2 for n>3) [March, pp. 484–487]

2. Reduction of the keto group to a methylene [March, pp. 1096–1098]

3. Amination of the free carboxylic acid group to an amide [March, pp. 371–374]

4. Friedel Crafts alkylation of the phenyl ring with 2-bromo-2-methylpropanoic acid [March, pp. 479–484]

5. Reduction of the amide to an amine [March, pp. 1099–1100]

6. Reduction of the phenyl ring to cyclohexyl [March, pp. 700–702]

Synthesis steps for Rigid Ring Amino Acids En where n=number of methylenes defined in FIG. 2:

1. Friedel Crafts mono alkylation of benzene with the structure $HOOC(CH_2)_mCBr(CH_3)_2$ (m=n) [March, pp. 479–484]

2. Friedel Crafts alkylation of the phenyl ring with 2-bromo-2-nitropropane [March, pp. 479–484]

3. Reduction of the nitro group to an amine [March, p. 1103]

4. Reduction of the phenyl ring to cyclohexyl [March, pp. 700–702]

Synthesis steps for Rigid Ring Amino Acids Fn where n=number of methylenes defined in FIG. 2:

1. Friedel Crafts mono alkylation of benzene with $HOOC(CH_2)_mCBr(CH_3)_2$ (m=n−1 for all n>0) [March, pp. 479–484]

2. Amination of the free carboxylic acid group to an amide [March, pp. 371–374]

3. Friedel Crafts alkylation of the phenyl ring with 2-bromo-2-methylpropanoic acid [March, pp. 479–484]

4. Reduction of the amide to an amine [March, pp. 1099–1100]

5. Reduction of the phenyl ring to cyclohexyl [March, pp. 700–702]

Synthesis steps for Rigid Ring Amino Acids Gn where n=number of methylenes defined in FIG. 2:

1. Friedel Crafts mono alkylation of benzyl alcohol with the structure $HOOC(CH_2)_mCBr(CH_3)_2$ (m=n−1 for n>0) [March pp. 479–484]

2. Amination of the free carboxylic acid group to an amide [March, pp. 371–374]

3. Oxidation of the alcohol group to a carboxyl group [March, p. 1084]

4. Reduction of the amide to an amine [March, pp. 1099–1100]

5. Reduction of the phenyl ring to cyclohexyl [March, pp. 700–702]

Synthesis steps for Rigid Ring Amino Acids Hn where n=number of methylenes defined in FIG. 2:

1. Friedel Crafts mono alkylation of benzene with $HOOC(CH_2)_mCBr(CH_3)_2$ (m=n) [March, pp. 479–484]

2. Nitration of the phenyl ring [March, pp. 468–470]

3. Reduction of the nitro group to an amine [March, p. 1103]

4. Reduction of the phenyl ring to cyclohexyl [March, pp. 700–702]

Some of the Rigid Ring Amino Acids have other synthesis routes which may be preferred. This is particularly the case for those with small n values such as n=0 or 1 or 2 or 3. For example, the structures E0 and F0 are identical and a preferred synthesis route would be two steps of Friedel Crafts alkylation of benzene: first mono alkylation with 2-bromo-2-methyl-propanoic acid and then alkylation with 2-bromo-2-nitropropane followed by nitro group reduction and then phenyl ring reduction. It is also noted that some choices for the value of n in FIG. 2 yield other pairs which are identical. For example for n=0, A0 is the same structure as B0, C0 is the same structure as G0, and D0 is the same structure as H0.

An additional benefit of the Rigid Ring Amino Acids in the sub-families C, D, E, F, G and H shown in FIG. 2 is the advantage given by the bulkiness of the dimethyl groups on a carbon atom adjacent to the ring. The steric effects of these groups aid in increasing the relative amounts of the desired 1,4 para substituted product versus the undesired 1,2 ortho substituted product [March, p. 459].

Some of the Rigid Ring Amino Acids in the family defined in FIGS. 1 and 2 have advantages over others. One of the major uses of this family of Rigid Ring Amino Acids is as monomers or comonomers in AB type nylons. The properties of polyamides made from the Rigid Ring Amino Acids are such that, in general, the cyclohexyl ring structure is preferred over the phenyl ring structure. In general, the cyclohexyl group provides higher melting points (Ridgway, op. cit.). In some applications and environments, the cyclohexyl unit also provides greater chemical stability than does the phenyl group.

As known to those in the field of polyamide polymerization, structures with aromatic amines are very difficult to polymerize by melt polymerization techniques. Therefore the general structures of An and Hn as shown in FIG. 2 in which the rigid ring unit is phenyl are undesirable for melt polymerization.

The 1,4 substituted cyclohexyl unit can have the conformation of cis or trans. The trans form is preferred. A desirable feature of the synthesis routes and polymerization conditions for these amino acids is maximization of the trans form of the cyclohexyl units in the final polyamide.

Polymerization of Rigid Ring Amino Acids:

Some monomers that are utilized to make polyamides of the AB type can exist as an amino acid or as the cyclic lactam of that amino acid. As used herein, any α,ω amino acid denoted as a monomer means equivalently its lactam. Two common such monomers are 6-aminohexanoic acid or its lactam, caprolactam, and 12-aminododecanoic acid or its lactam, laurolactam.

Melt polymerization and/or solid state polymerization are preferred processes for polymerization of the Rigid Ring Amino Acids of this invention. The polymerization or copolymerization of the amino acids of this invention can be done utilizing the conventional polymerization techniques for AB polyamides as noted in Kohan (pp. 24–41).

Two or more Rigid Ring Amino Acids can be utilized as comonomers with themselves as well as comonomers with aliphatic amino acids.

Prior Art:

The prior art of this class of amino acids and their polyamides are 2-(4-aminocyclohexyl)ethanoic acid and 4-(aminomethyl)cyclohexanecarboxylic acid which are isomorphic with 6-aminohexanoic acid [Kohan p. 372]. In addition, some related structures of cyclohexyl based amino acids with relatively short methylene lengths are known such as 4-(2-aminoethyl) cyclohexanecarboxylic acid noted in U.S. Pat. Nos. 3,998,947 and 4(4-aminocyclohexyl)butanoic acid.

GENERAL REFERENCES

Kohan, Melvin I. ed., "Nylon Plastics Handbook"; Hanser/Gardner Publications Inc., Cincinnati (1995)
March, Jerry; "Advanced Organic Chemistry"; 3rd Edition; John Wiley and Sons, New York (1985)

The invention claimed is:

1. A Rigid Ring Amino Acid having the chemical structure

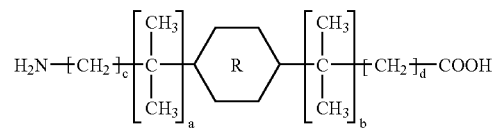

wherein R is cyclohexyl and having the parameters a, b, c, and d wherein the parameters a and b may be chosen to be 0 or 1 and wherein the parameters c and d are chosen to be n where n is an integer and further chosen such that for any integer value of c=n where n is greater than zero then d=0 and for any integer value of d=n where n is greater than zero then c=0 and wherein the Effective Methylene Length of the Rigid Ring Amino Acid is greater than 8 and less than 18 and the Carbon Number of the Rigid Ring Amino Acid is greater than 11 and less than 25.

2. The Rigid Ring Amino Acid of claim 1 wherein the parameter a or b or both a and b are 1.

3. A Rigid Ring Amino Acid having the chemical structure

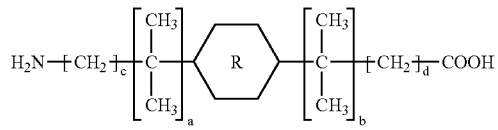

wherein R is cyclohexyl and having the parameters a and b may be chosen to be 0 or 1 and wherein a, b, c, and d wherein the parameters a or b or both are 1 and wherein the parameters c and d are chosen to be n where n is an integer and further chosen such that for any integer value of c=n where n is greater than zero then d=0 and for any integer value of d=n where n is greater than zero then c=0 and wherein the Rigid Ring Amino Acid has an Effective Methylene Length greater than 4 and less than 18 and a Carbon Number greater than 9 and less than 25.

* * * * *